United States Patent [19]

Brinkman et al.

[11] Patent Number: 4,965,112
[45] Date of Patent: Oct. 23, 1990

[54] METHOD FOR APPLYING A BLOOD-COMPATIBLE COATING TO POLYETHER-URETHANE MOULDED ARTICLES AND THE POLYMETHER-URETHANE MOULDED ARTICLES COATED IN THIS WAY

[75] Inventors: Egbert Brinkman; Adriaan Bantjes, both of Enschede, Netherlands

[73] Assignee: Stichting Voor de Technische Wetenschappen, Utrecht, Netherlands

[21] Appl. No.: 317,677

[22] Filed: Mar. 1, 1989

[30] Foreign Application Priority Data

Mar. 8, 1988 [NL] Netherlands ............... 8800577

[51] Int. Cl.⁵ .............................. B29D 23/00
[52] U.S. Cl. ........................ 428/36.91; 427/2; 427/54.1; 427/393.5; 428/376; 428/398; 604/264; 604/269; 604/280

[58] Field of Search .......... 427/2, 54.1, 393.5; 604/96, 264, 269, 280; 428/413, 423.1, 36.91, 376, 398

[56] References Cited

U.S. PATENT DOCUMENTS 4,743,258  5/1988  Ikata et al. ............... 427/2 X

FOREIGN PATENT DOCUMENTS 8602087  4/1986  PCT Int'l Appl. .

Primary Examiner—Michael Lusignan
Attorney, Agent, or Firm—Rosen, Dainow & Jacobs

[57] ABSTRACT

The invention relates to a method for applying a blood-compatible polyethlene oxide coating to polyether-urethane moulded articles like catheters, for instance oxygen sensor catheters. The so obtained blood-compatible articles may advantageously be used in the case of long-term contact with blood or body tissue.

11 Claims, 1 Drawing Sheet

METHOD FOR APPLYING A BLOOD-COMPATIBLE COATING TO POLYETHER-URETHANE MOULDED ARTICLES AND THE POLYMETHER-URETHANE MOULDED ARTICLES COATED IN THIS WAY

The invention relates to the application of a blood-compatible coating to polyether-urethane moulded articles such as catheters, in particular oxygen sensor catheters and also many other articles for biomedical applications which come into contact with the blood in use, and to the polyether-urethane moulded articles coated in this way.

As is generally known, polyether-urethanes have found application in numerous biomedical fields by virtue of their good physical and mechanical properties and also their relatively good compatibility with blood. However, it has been found that for the vast majority of these polyether-urethane elastomers this compatibility with blood still leaves something to be desired for certain applications, in particular in the case of long-term contact with blood or body tissue. It is in particular the surface, or more accurately the surface characteristics, of the moulded articles which play a significant, if not decisive, role here. Specifically, the surface of exogenic materials must possess an adequate resistance to blood coagulation, blood platelet adhesion etc. on contact with body tissues and blood. Thrombogenesis, embolization and the like are, therefore, frequently the cause which makes the application of biomedical moulded articles doomed to failure.

More particularly, the use of the majority of non-physiological biomaterials such as polyether-urethanes after contact with, for example, blood gives rise within a very short time to a thin protein-like layer on these materials, which layer is rich in fibrinogen, fibronectin and gamma-globulin. By reason of the circulation of the blood, further protein components will adhere firmly to this initially thin layer, so that phenomena can arise which lead to activation of the defence mechanism, such as coagulation, blood platelet adhesion, adhesion of white blood cells and the like.

In view of the disadvantages, described above, of the use of synthetic biomedical materials, methods for eliminating or greatly reducing the undesired phenomena associated with the use of moulded articles produced from these biomedical materials has been diligently sought.

One of the methods was directed towards the modification of the surface of biomedical materials, polyether-urethanes in the present case, to attempt to prevent the endogenic protein adhesion and agglomeration.

The process known from EP-A-0,061,312 for the application of covalently bonded aliphatic chains with 14-30 carbon atoms to the substrate surface, for example of polyurethane, is mentioned as one of the methods. Preferably, n-octadecyl groups are attached to the polymer substrate surface. Coated substrates of this type possess selective and apparently reversible bonding sites for albumin, so that the adherence of thrombogenic proteins is largely prevented. Five methods for the covalent bonding of the long aliphatic chains to the substrate surface are described in this EP-A-0,061,312, a proton-removing base such as sodium ethoxide (NaOEt), sodium t-butyrate (NaO.t.Bu), potassium hydride or sodium hydride and methyl magnesium bromide always having to be used.

In view of the specific but somewhat laborious methods of preparation of polymer substrates coated with alkyl groups having 14-30 carbon atoms known from EP-A-0,061,312, the Applicant has sought for a method which is simple in respect of technique for immobilizing a synthetic polymer layer on a polyether-urethane moulded article which possesses an outstanding compatibility with blood.

It has been found that the aim of the invention can be achieved when a layer of polyethylene oxide with a $M_w$ in the range of 1,500-1,500,000, preferably 100,000-300,000, is applied directly to a polyether-urethane moulded article and the polyethylene oxide layer applied is then linked to the polyether-urethane moulded article. Surprisingly, very simple techniques, such as a heat treatment or irradiation with UV light, can be used for this linking.

More particularly, the thermal linking according to the invention is carried out at a temperature in the range of 80-180° C., preferably 100-150° C. Advantageously, the thermal linking is carried out in the presence of an organic peroxide which can be used at this temperature, for example of the formula R—O—O—R' in which R and R' independently of one another represent a straight-chain or branched alkyl group with 4-10 carbon atoms, a cycloalkyl group with 5-8 carbon atoms or an aralkyl group with 6-10 carbon atoms. Dicumyl peroxide is mentioned as an example of a peroxide which can be used.

The great advantage of the thermal linking lies in the possibility for also providing internal surfaces of polyether-urethane moulded articles such as catheters with a coating layer which is compatible with blood.

A second simple linking method relates to the use of UV light (10-400 nm and advantageously 240-300 nm). Specifically, it has been found that an outstanding adhesion between the polyetherurethane moulded article and the polyethylene oxide coating is produced by the simple use of this type of light. Advantageously an organic peroxide, for example of the formula R—O—O—R', is also used with this method, R and R' independently of one another representing a straight-chain or branched alkyl group with 4-10 carbon atoms, a cycloalkyl group with 5-8 carbon atoms or an aralkyl group with 6-10 carbon atoms. Dicumyl peroxide can be mentioned, for example, as a suitable peroxide for this linking method. The advantage of the use of a peroxide of this type lies, specifically, in the fact that a polyethYlene oxide coating with optimum characteristics is obtained in the same reaction time as with the method without peroxide catalyst. The UV light itself can be generated with the aid of a simple mercury lamp (254 nm) or otherwise.

The polyether-urethanes which can be used are the materials which are known from the state of the art and are used in the biomedical field. More particularly, such materials are made up of a polyether segment and a polyurethane segment and during the preparation of such materials use is frequently made of a chain extender such as an alkane diol or alkylene diamine. The material "Pellethane 2363" (Upjohn Co.), which essentially is made up of polytetramethylene oxide and 4, 4'-diphenylmethane diisocyanate with butane-1, 4-diol as the chain extender, is mentioned as an example of a polyether-urethane obtainable commercially. Other examples of commercially available polyether-urethanes are the "Biomer" materials (Du Pont de Nemours & Co.), "Cardiothane" (Kontron Cardiovascular Inc. USA), "Tecoflex" (Mitra Medical International Inc. USA), and "Esthane" (Goodrich, USA).

The polyethylene oxide is used as a solution in a suitable solvent, such as dichloromethane, ethyl acetate, acetone, chloroform, methyl ethyl ketone or dichloroethane, in a concentration of, for example, 0.5–10% (weight/vol, as kg/l), preferably 1–5 (weight/vol). The polyethylene oxide solution, in which a suitable organic peroxide may or may not be incorporated, is applied to the polyether-urethane moulded article by means of dipping, spraying and the like. After drying, for example in air for 1–5 hours and preferably 1–2 hours, the samples are subjected to the thermal linking method or the UV light linking method. After this treatment the samples are washed with an excess of solvent, such as twice distilled water and acetone, in order to remove non-linked polyethylene oxide and possible other by-products, for example the peroxide which may have been used.

As indicated above, the coated polyether-urethane surfaces according to the invention possess an outstanding compatibility with blood. The following methods were used for the characterization of the polyether-urethane surfaces modified in accordance with the invention.

(1) The "captive bubble" technique.

Figure 1:
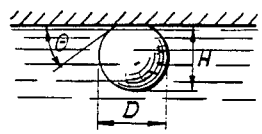
FIG. 1-Air bubble showing a contact angle.

With the aid of this technique the degree of hydrophilicity of surfaces can be determined. This technique comprises the following steps:

(a) the samples are dried in a vacuum oven (T=60° C.) for 1 night;
(b) after drying, the samples are placed upside down in a bath of twice-distilled water, after which the sample is allowed to equilibrate for 1 hour;
(c) subsequently, an air bubble is introduced with the aid of a microsyringe, immediately after which a photograph is taken (see FIG. 1);
(d) the contact angle, as expressed in the following formula with the symbols given in FIG. 1:

$$\Theta = \cos^{-1}\left(\frac{2H}{D} - 1\right)$$

gives the degree of the hydrophilicity of the surface examined (this method is described in King R.N., Andrade J. et al., J. of Colloid and Interface Science, 103, 62 (1985)).

(2) Blood platelet adhesion.

In the case of the in vitro evaluation, the blood platelet adhesion to the polyether-urethane surfaces coated in accordance with the invention is determined. For this investigation both tests with blood platelets in buffer and with blood platelets in plasma are carried out.

The perfusion experiments used with this blood platelet adhesion technique are given in Poot A., Procedure voor het Wassen van Humane Bloedplaatjes volgens J.P. Casenave e.a. (Procedure for washing human blood platelets according to J.P. Casenave e.a.), internal publication, University of Twente (1984). More particularly, the following steps can be differentiated per test:

(A) isolation of the blood platelets;
(B) washing of the blood platelets;
(C) perfusate preparation;
(D) perfusion; and
(E) blood platelet adhesion determination.

Re (A): The plasma rich in blood platelets is obtained by centrifuging blood with an ACD (acidic citrate dextrose) anticoagulant for 15 minutes at 175 g. The plasma rich in blood platelets is pipetted off and then centrifuged (1570 g, 13 min). Finally, the plasma is drawn off with a pipette.

Re (B): Washing of the blood platelets is carried out as follows:

(a) the blood platelets are suspended in a Hepes-buffered Tyrode Albumin (HBTA) solution;
(b) after an incubation time of 15 minutes at 37° C. a centrifuge treatment takes place at 1100 g for 10 minutes;
(c) the product obtained is resuspended in 10 ml HBTA solution, after which the above washing procedure is repeated;
(d) the blood platelets pellet obtained is then resuspended in 10 ml HBTA solution.

Labelling of the blood platelets takes place during the first washing step by adding $10\mu Ci^{xxx}$ In oxinate per ml.

Re (C): Three perfusates containing 180,000 blood platelets/$\mu$l are prepared, i.e.:

(1) a perfusate made up of blood platelets, washed in the above manner, in a HBTA buffer;
(2) a perfusate made up of blood platelets, washed in the above manner, resuspended in plasma; and
(3) a perfusate as perfusate (2) but with the addition of 1 $\mu$M $Ca^{2+}$ ionophore per liter just before the perfusion experiment. The fact is that the anticoagulant used (citrate) binds calcium ions, as a result of which the activity of the platelets is reduced. This effect is compensated for with $Ca^{2+}$ ionophore.

Figure 2:
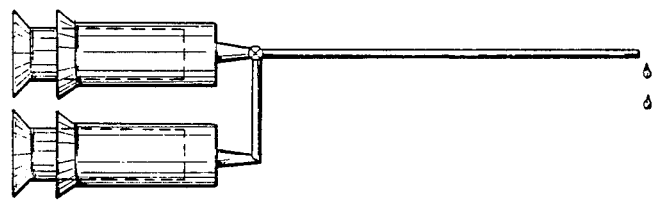
FIG. 2-Perfusion system with upper and lower pump.

Re (D): The perfusion is carried out with the aid of the perfusion system shown in FIG. 2. The procedure employed is as follows:

(1) the capillary tubes with an internal diameter of 0.8 mm are flushed through for 10 minutes with twice-distilled water (shear rate: 1000 $s^{-1}$) and then filled with a HBTA solution (via the lower pump in FIG. 2);
(2) the particular perfusate is pumped through the capillary tube for 5 minutes at 300 $s^{-1}$ (via the upper pump in FIG. 2); and
(3) the capillary tube is finally rinsed with a HBTA solution for 5 min at 1000 $s^{-1}$ (via the lower pump in FIG. 2).

Re (E): The determination of the blood platelet adhesion is carried out by dividing the capillary used into three 2-cm segments, the ends of the capillary being removed. The radioactivity is then determined per segment. In the following examples to illustrate the invention films of Pellethane 2363 80A (Upjohn Co.) were used which were prepared in the following manner:

(1) the Pellethane 2363 80A is dissolved in tetrahydrofuran (5% by weight);
(2) the polymer solution obtained is poured into a Petri dish, after which the solvent evaporates slowly;
(3) after 3 days samples with a surface area of 8 cm$^2$ are cut from the film obtained and are extracted for 24 hours in methanol;
(4) the samples finally obtained are dried in air and then placed in a vacuum oven (T=60° C.) for 1 night.

The contact angle which was determined in the manner defined above for these films used as starting material was 64°.

The invention is illustrated with the aid of the following examples, which must be regarded as non-restrictive.

EXAMPLE I

A Pellethane 2363 80A film obtained in the above manner was dipped for 30 sec in a 1% by weight solution of polyethylene oxide in dichloromethane. The polyethylene oxide used had a $M_w$ of 180,000 (Polysciences, Warrington, USA). The Pellethane films were then dried in air for 1.5 hours. The samples were then irradiated for 1 hour with a UV lamp (254 nm) in order to initiate the linking reaction. After the irradiation, the treated films were washed with excess twice-distilled water in order to remove non-linked polyethylene oxide and with excess acetone in order to remove radical products.

The contact angle which was determined in the manner defined above for the treated Pellethane films was 34±4°.

EXAMPLE II

The procedure according to Example I was repeated except that in place of a 1% by weight solution of polyethylene oxide in dichloromethane, a 1% by weight solution of polyethylene oxide/dicumyl peroxide (95/5 w/w) in dichloromethane was used. The dicumyl peroxide was obtained from Schuchardt (West Germany).

After carrying out the method described in Example I, a film was obtained which had a contact angle of 30±3°.

EXAMPLE III

In accordance with this example Pellethane 2363 80A films were dipped for 30 sec into a 1% by weight solution of polyethylene oxide with a $M_w$ of 180,000 (Polysciences, Warrington, USA) in dichloromethane and then dried in air for 1.5 hours. The films were then heated in an oven for 2 hours at 140° C. and 1 hour at 130° C. The coated films were then washed with water and finally with acetone.

The contact angle of the sample was 37±3°.

EXAMPLE IV

The procedure according to Example III was repeated except that in place of a 1% by weight solution of polyethylene oxide in dichloromethane, a 1% by weight solution of polyethylene oxide/dicumyl peroxide (95/5 w/w) in dichloromethane was used. The dicumyl peroxide was obtained from Schuchardt (West Germany).

The contact angle of the sample obtained according to this example was 30±3°.

EXAMPLE V

Tests were carried out in accordance with the blood platelet adhesion technique described above using capillaries which were treated in accordance with the method described in Examples I–IV for the treated and untreated Pellethane 2363 80A films. The polyethene product PT.51 (Thalas B.V., The Netherlands) was also used as further comparison material.

The data obtained are summarized in Tables D–F below, Table D showing the blood platelet adhesion from a HBTA buffer, Table E the blood platelet adhesion from plasma and Table F the adhesion of activated blood platelets from plasma after the addition of $Ca^2$+ionophore. The expression "Pell 80A" relates to a Pellethane 2363 80A film.

TABLE D

Blood platelet adhesion from buffer: (perfusate 1)

| Material | Number of platelets per $cm^2$ |
|---|---|
| Pell 80A | 276,000 ± 28,000 |
| Pell 80A after extraction with methanol and inoculating with PEO 180,000 (in accordance with the method according to IV) | 12,000 ± 4,000 |
| Polyethene | 422,000 ± 99,000 |

TABLE E

Blood platelet adhesion from plasma: (perfusate 2)

| Material | Number of platelets per $cm^2$ |
|---|---|
| Pell 80A | 115,000 ± 33,000 |
| Pell 80A after extraction with methanol and inoculating with PEO 180,000 (in accordance with the method according to Ex. IV) | 6,000 ± 4,000 |
| Pell 80A after extraction with methanol and inoculating with PEO 300,000 (in accordance with the method according to Ex. IV) | 12,000 ± 3,000 |
| Pell 80A after extraction with methanol and inoculating with PEO 600,000 (in accordance with the method according to Ex. IV) | 15,000 ± 3,000 |
| Polyethene | 719,000 ± 139,000 |

TABLE F

Adhesion of activated blood platelets from plasma after the addition of $Ca^2$ + ionophore: (perfusate 3)

| Material | Number of platelets per $cm^2$ |
|---|---|
| Pell 80A | 150,000 ± 15,000 |
| Pell 80A after extraction with methanol and inoculating with PEO (Mw 180,000 in accordance with the method according to IV) | 30,000 ± 4,000 |
| Polyethene | 3,800,000 ± 500,000 |

I claim:

1. Method for applying a blood-compatible coating to a polyether-urethane moulded article, characterized in that a layer of polyethylene oxide with a weight average molecular weight in the range of 1,500–1,500,000 is applied to the polyether-urethane moulded article using heat treatment or irradiation and the polyethylene oxide layer applied is then linked to the polyethylene-urethane moulded article.

2. Method according to claim 1, characterized in that polyethylene oxide with a molecular weight in the range of 100,000–300,000 is used.

3. Method according to claim 1 or 2, characterized in that the linking is carried out thermally at a temperature in the range of 80–180° C.

4. Method according to claim 3, characterized in that the linking is carried out thermally at a temperature in the range of 100–150° C.

5. Method according to claim 3 or 4, characterized in that the linking is carried out in the presence of an organic peroxide of the formula R—O—O—R', in which R and R' independently of one another represent an alkyl group with 4–10 carbon atoms, a cycloalkyl group with 5–8 carbon atoms or an alkaryl group with 6–10 carbon atoms.

6. Method according to claim 5, characterized in that the linking is carried out in the presence of dicumyl peroxide.

7. Method according to claim 1 or 2, characterized in that the linking is carried out with the use of UV light.

8. Method according to claim 7, characterized in that the linking is carried out with the use of UV light in the range of 240–300 nm.

9. Method according to claim 7 or 8, characterized in that the linking is carried out in the presence of an organic peroxide of the formula R—O—O—R', in which R and R' independently of one another represent an alkyl group with 4–10 carbon atoms, a cycloalkyl group with 5–8 carbon atoms or an alkaryl group with 6–10 carbon atoms.

10. Method according to claim 9, characterized in that the linking is carried out in the presence of dicumyl peroxide.

11. Polyether-urethane moulded article, such as a catheter, provided with a polyethylene oxide coating applied in accordance with the method according to one of claims 1–10.

* * * * *